(12) United States Patent
Kolster

(10) Patent No.: US 7,468,068 B2
(45) Date of Patent: Dec. 23, 2008

(54) SUTURE FOR WOUND CLOSURE, TISSUE APPROXIMATION, TISSUE SUPPORT, SUSPENSION AND/OR FIXATION

(76) Inventor: Alwin Kolster, 3185 Palisades Dr., Corona, CA (US) 92882

( * ) Notice: Subject to any disclaimer, the term of this patent is extended or adjusted under 35 U.S.C. 154(b) by 351 days.

(21) Appl. No.: 11/168,173

(22) Filed: Jun. 28, 2005

(65) Prior Publication Data

US 2006/0079935 A1    Apr. 13, 2006

Related U.S. Application Data

(60) Provisional application No. 60/584,927, filed on Jun. 30, 2004.

(51) Int. Cl.
*A61B 17/04* (2006.01)
(52) U.S. Cl. .................................. 606/228
(58) Field of Classification Search ............. 606/228
See application file for complete search history.

(56) References Cited

U.S. PATENT DOCUMENTS

| | | | | |
|---|---|---|---|---|
| 5,584,859 | A | * | 12/1996 | Brotz ............... 606/228 |
| 5,984,933 | A | * | 11/1999 | Yoon ............... 606/148 |
| 6,102,947 | A | * | 8/2000 | Gordon ............... 623/13.11 |
| 2003/0149447 | A1 | * | 8/2003 | Morency et al. ............... 606/228 |
| 2004/0138683 | A1 | * | 7/2004 | Shelton et al. ............... 606/151 |
| 2004/0138704 | A1 | * | 7/2004 | Gambale et al. ............... 606/213 |
| 2007/0219587 | A1 | * | 9/2007 | Accardo ............... 606/228 |

* cited by examiner

*Primary Examiner*—Darwin P Erezo
*Assistant Examiner*—Naveen K Singh
(74) *Attorney, Agent, or Firm*—Willie Krawitz

(57) ABSTRACT

A suture assembly includes an elongated flexible body supporting a plurality of frusto-conically shaped tissue-engaging elements in a generally spaced arrangement thereon. A curved body having a sharp point is joined to one end of the flexible body while a straight pointed body is joined to the remaining end of the flexible body. In alternate embodiments, the tissue-engaging elements are elliptical or polygonal in cross-section. In a still further alternate embodiment, the tissue-engaging elements are divided into first and second oppositely facing sets to provide a bidirectional suture.

8 Claims, 5 Drawing Sheets

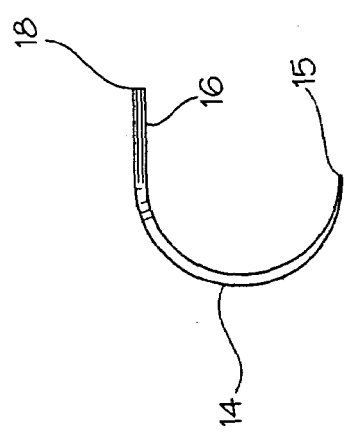
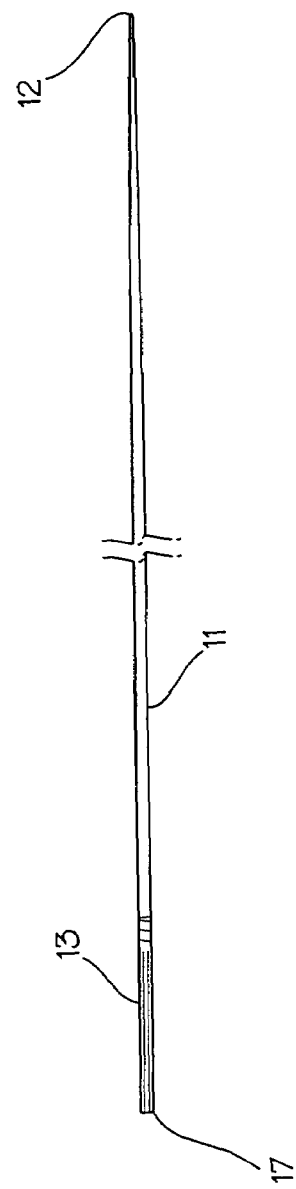
FIG. 7
FIG. 6

SUTURE FOR WOUND CLOSURE, TISSUE APPROXIMATION, TISSUE SUPPORT, SUSPENSION AND/OR FIXATION

CROSS-REFERENCE TO RELATED APPLICATIONS

This application claims the benefit of and priority under 35 U.S.C. 119(e) of U.S. Provisional Patent Application No. 60/584,927 filed Jun. 30, 2004 as incorporated herein by reference.

FIELD OF THE INVENTION

This invention relates generally to apparatus for tissue suturing and particularly to apparatus for surgical incision or wound closure as well as tissue approximation in surgical procedures such as cosmetic surgery.

BACKGROUND OF THE INVENTION

A substantial number of devices have been provided throughout the years which may be used for closure of a wound or surgical incision. Such devices have included staples, sewing and stitching as well as tissue connecting sutures.

One recently developed type of suture may be generally described as a "barbed suture". Such sutures generally comprise elongated thin filaments having pluralities of tissue-engaging barbs and are designed for closure of wounds or surgical incisions. In such use, the main filament applies drawing tension while the pluralities of tissue-engaging barbs increase the "grip" of the suture to the drawn tissue.

Not surprisingly, the need for ever-improved sutures has prompted practitioners in the art to provide a variety of suture structures which can be generally described as barbed sutures. For example, U.S. Pat. No. 3,123,077 issued to Alcamo sets forth a SURGICAL SUTURE having an elongated flexible filament defining a plurality of outwardly extending barbs or projections formed on its surface.

U.S. Pat. No. 6,241,747 issued to Ruff sets forth a BARBED BODILY TISSUE CONNECTOR having an elongated filament or body which supports a plurality of closely spaced barbs disposed along the body. The barbs are pointed in a first direction on one portion of the body and in an opposite direction on the remaining portion of the body.

U.S. Pat. No. 5,425,747 issued to Brotz sets forth a SUTURE formed of a bioabsorbable material having a central body defining a plurality of lateral members extending perpendicularly therefrom in the same general plane with the central body. Each lateral member further defines a plurality of barb members extending at acute angles therefrom. The lateral members are constructed to be inserted laterally into two sides of a tissue cut and to provide a securely retained structure.

U.S. Pat. No. 5,584,859 issued to Brotz sets forth a SUTURE ASSEMBLY formed of a bioabsorbable material having a central body member and a plurality of elongated members in a plane extending perpendicularly on each side therefrom. The extending lateral members are interconnected to the central body member by connectors and each support a plurality of acutely angled barb members extending from their respective outer surfaces.

While the foregoing described prior art devices have to some extent improved the art and in some instances enjoyed commercial success, there remains nonetheless a continuing need in the art for evermore improved tissue sutures.

SUMMARY OF THE INVENTION

Accordingly, it is a general object of the present invention to provide an improved apparatus for tissue suturing. It is a more particular object of the present invention to provide an improved apparatus for wound closure, tissue approximation, tissue support, suspension and/or fixation. It is a still more particular object of the present invention to provide an improved suture apparatus which is particularly advantageous in cosmetic surgery procedures directed toward recently emerging nonsurgical minimally invasive cosmetic surgery procedures directed toward facial lifting and contouring.

Thus, the inventive suture structure of the present invention provides an implantable directional camming device which may be fabricated in either a directional or bi-directional structure. The suture apparatus of the present invention may be formed of elements which are injection molded or cold-headed and may be used for wound closure, tissue approximation, tissue support, suspension and/or fixation. The molded or cold-headed elements may be formed having either generally circular or elliptical cross-sections as desired. The suture of the present invention is constructed to be implanted into the human body with or without the use of an introducer and is designed to work in conjunction with the healing process post surgical such as scar tissue formation and fibrosis. The inventive suture apparatus holds wounds closed or fixates tissue without the need for suture knot tying to maintain tissue approximation. The inventive structure being formed of injection molded or cold-headed elements may be formed without the need for conventional machine cutting to provide tissue-gripping structure.

Thus, in accordance with the present invention, there is provided a suture comprising: an elongated flexible body having first and second ends; a plurality of tissue-engaging elements each defining a bore therethrough, the tissue-engaging elements received upon the elongated flexible body; and a plurality of knots tied in the elongated flexible body each larger than the bore, the knots maintaining the tissue-engaging elements in a serial arrangement on the elongated flexible body.

In further accordance with the present invention, there is provided a suture assembly comprising: an elongated needle body having a first pointed end and a first connector end; a curved needle body having a second pointed end and a second connector end; an elongated filament having a first end joined to the first connector end, a second end joined to the second connector end, and a plurality of knots formed in the filament; and a plurality of tissue-engaging elements each defining a bore therethrough, the tissue-engaging elements being received upon the filament by passing the filament through the bores with each tissue-engaging element being proximate one of the knots.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

FIG. 6 sets forth a side view of the straight needle portion of the present invention suture assembly;

FIG. 7 sets forth a side view of the curved needle portion of the present invention suture assembly;

DESCRIPTION OF THE PREFERRED EMBODIMENT

Figure 1:
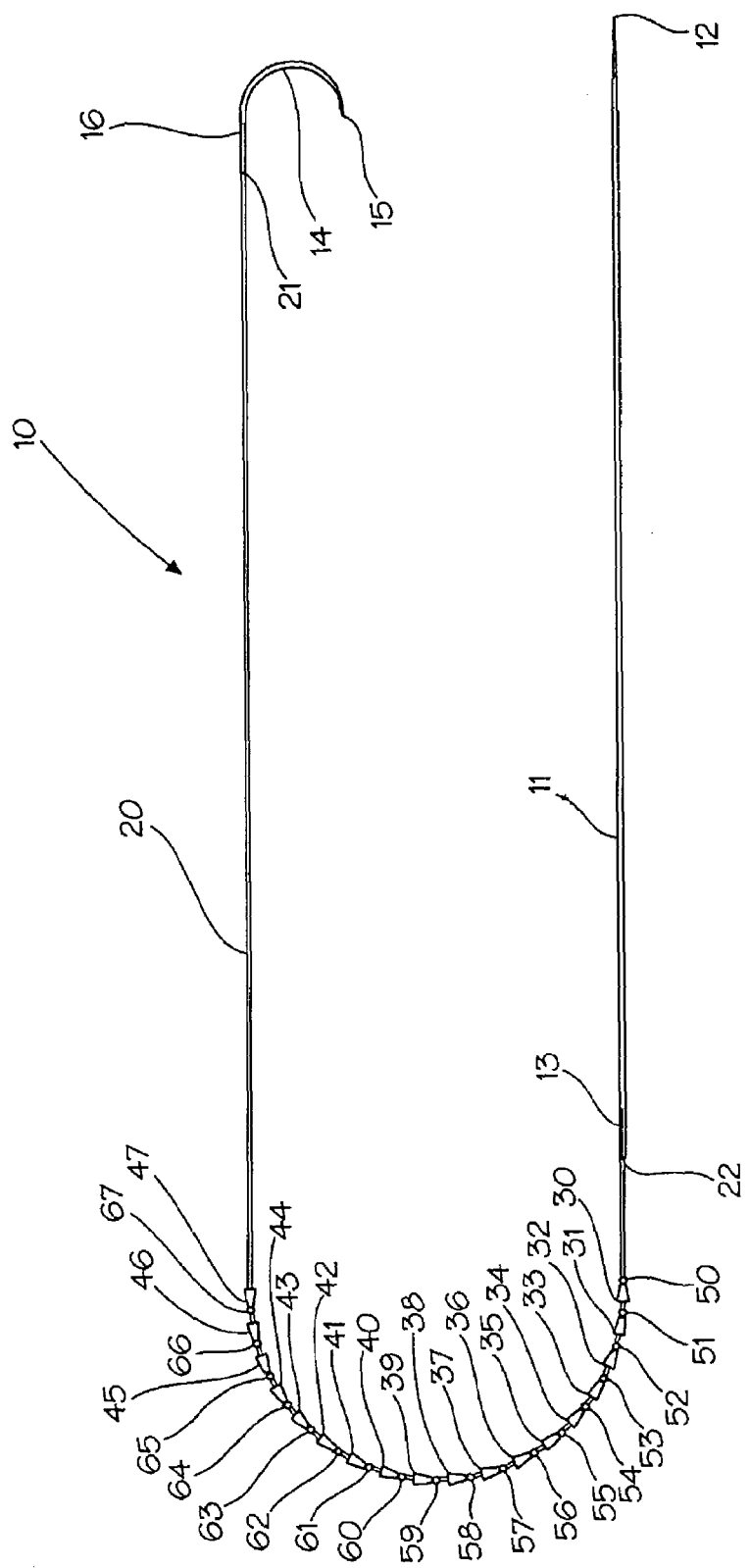
FIG. 1 sets forth a side view of a complete suture assembly constructed in accordance with the present invention.

FIG. 1 sets forth a side view of a suture assembly constructed in accordance with the present invention and generally referenced by numeral 10. By way of overview, suture assembly 10 comprises four basic elements which are a generally straight body 11, a flexible elongated body 20, a plurality of tissue-engaging elements 30 through 47 and a curved body 14. More specifically, suture assembly 10 includes an elongated straight body 11 formed of a plastic material such as polypropylene or the like and includes a generally pointed end 12 and a connector end 13. Suture assembly 10 further includes a flexible elongated filament body 20 having an end 22 secured to connector 13 in the manner described below. Flexible body 20 further supports a plurality of tissue-engaging elements 30 through 47 set forth below in greater detail in FIGS. 4 and 5. Suffice it to note here that tissue-engaging elements 30 through 47 are substantially identical in structure and are received upon flexible body 20. In addition, tissue-engaging elements 30 through 47 comprise generally conical structures which impart a directional character to the suture assembly in its engagement of tissue. As is better seen in FIG. 3, flexible body 20 further defines a plurality of tied knots 50 through 67 which are tied within flexible body 20 to provide limitation of the movement of tissue-engaging elements 30 through 47 upon flexible body 20. Flexible body 20 further defines an end 21 which is received within a connector 16 of curved body 14. Curved body 14 further defines a sharp pointed end 15. Connectors 13 and 16 secure ends 22 and 21 of flexible body 20 by use of a conventional crimping attachment.

As mentioned above, the present invention suture assembly is suitable for use in a variety of wound closure, tissue approximation, tissue support, suspension and/or fixation procedures. However, as is also mentioned above, the present invention suture assembly is particularly well suited to use in procedures which involve face-lifting or contouring during cosmetic surgery procedures. During such use, the directional grip or directional character provided by tissue-engaging elements 30 through 47 further enhance the lifting and contouring capability of the suture. In its preferred fabrication, the entire suture is formed of a monofilament material such as polypropylene or the like. Alternatively, an absorbable material such as PDF may be used. Once inserted under the skin, the directional character of tissue-engaging elements 30 through 47 form a permanent support structure for the tissue and actually lift and contour the tissue. While not limited to use in any particular procedure, the present invention suture is well suited to use for lifting and contouring nasolabral lines (smile lines) as well as retracting of the patient's jowls or other parts of the body which need lifting or contouring. The procedure utilizing the present invention suture is extremely safe and requires relatively little time compared to conventional cosmetic surgery. The procedure utilizing the present invention suture may be performed under local anesthesia with the patient remaining comfortably awake. During the procedure, the suture is inserted deep into the subcutaneous tissue along the lines where the new contour is desired. Typically, as few as three suture insertions significantly raise the cheek contour while as few as two sutures correctly placed may be utilized to draw back the patient's jowls. The suture may also be used to raise the patient's brow and pull back neck tissue. Also, the present invention suture may be used elsewhere such as pulling in waist lines. Once inserted, the gripping power and lifting effect of the tissue is maximized after several months when the collagen of the patient's tissue has formed around the tissue-engaging elements.

It will be apparent to those skilled in the art that the number of tissue-engaging elements utilized in the present invention suture assembly is to some extent a matter of choice and may readily be varied for suitability to specific applications or uses. Thus, the number of tissue-engaging elements shown in FIG. 1 should be regarded as illustrative of the principles of operation of the present invention suture assembly and not as limitation as to the inventive structure.

Figure 2:
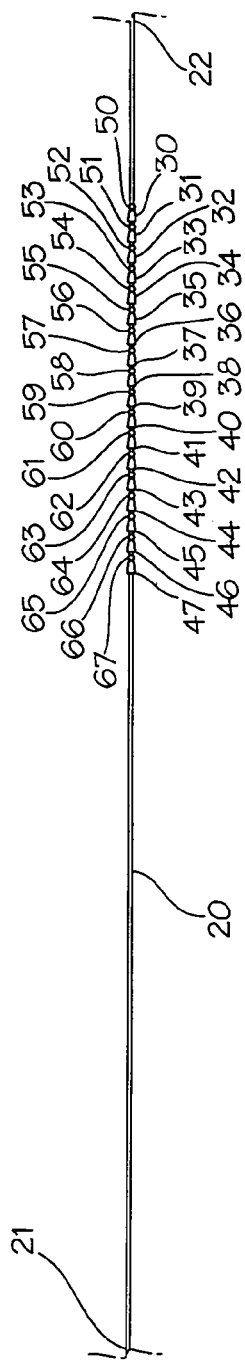
FIG. 2 sets forth a side view of the suture portion of the present invention suture assembly.

FIG. 2 sets forth a side view of the suture portion of suture assembly 10. As described above, the present invention suture includes an elongated flexible preferably monofilament body 20 formed of a material such as polypropylene or the like. Flexible body 20 defines an end 21 and an end 22. A plurality of tissue-engaging elements 30 through 47 are threaded upon flexible body 20. As is better seen below in FIG. 3, flexible body 10 is tied to define a plurality of knots (knots 50 through 67 shown in FIG. 1). Knots 50 through 67 are positioned upon flexible body 20 at generally evenly spaced intervals and are utilized in limiting the movement of tissue-engaging elements 30 through 47 upon flexible body 20. Thus, it will be apparent that tissue engaging elements 30 through 67 are serially placed upon flexible body 20 and that a corresponding plurality of knots 50 through 67 are tied in front of each tissue-engaging element as it is threaded upon end 22 of flexible body 20. For example, assembly of tissue-engaging elements 30 through 47 upon flexible body 20 is initiated by threaded tissue-engaging element 47 passed end 22 to the desired position on body 20. Thereafter, knot 67 is tied in flexible body 20. Next, tissue engaging element 67 is threaded upon end 22 of flexible body 20 and positioned in proximity to tissue engaging element 47. Thereafter, flexible body 22 is tied to form knot 66. This procedure continues as each tissue-engaging element is threaded upon end 22 of flexible body 20 and thereafter moved into proximity of the preceding tissue-engaging element after which the corresponding positioning knot is tied in flexible body 20. Once all of the desired tissue-engaging elements have been assembled to flexible body 20 and the corresponding travel limiting knots have been tied within flexible body 20, flexible body 20 is ready for assembly to straight body portion 11 and curved body portion 14 (seen in FIG. 1) to complete the suture.

Figure 3:
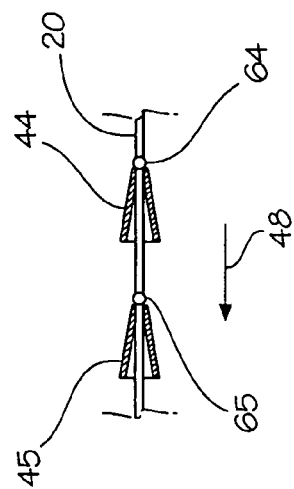
FIG. 3 sets forth a section view of an illustrative segment of the tissue-gripping portion of the present invention suture.

FIG. 3 sets forth an enlarged view of a portion of flexible body 20 having section views of tissue-engaging elements 44 and 45 secured thereon in the manner described above. Thus, in the example of FIG. 3, flexible body 20 is shown supporting tissue engaging elements 44 and 45. Correspondingly, flexible body 20 has been tied to form a pair of knots 65 and 64 each of which limit the positions of corresponding of tissue-engaging elements 44 and 45. In this manner, tissue-engaging elements 44 and 45 are able to transfer drawing force from flexible body 20 to surrounding tissue which is engaged by elements 44 and 45. Once again, it will be noted that this engagement is directional in that elements 44 and 45 provide substantial greater engagement of tissue in the direction indicated by arrow 48.

Figure 4:
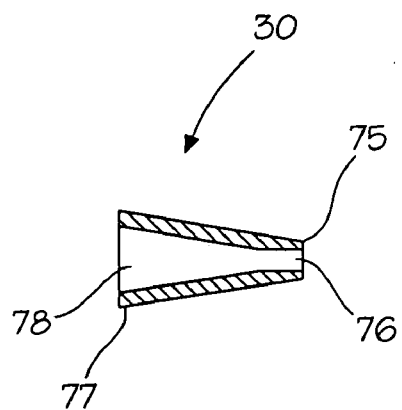
FIG. 4 sets forth a section view of a tissue-gripping element prior to installation in the suture assembly.

FIG. 4 sets forth a section view of tissue-engaging element 30. It will be apparent to those skilled in the art that tissue-engaging elements 30 through 47 (seen in FIG. 1) are substantially identical in construction. Thus, FIG. 4 and the descriptions which are provided in conjunction therewith will be understood to apply equally well to tissue-engaging elements 31 through 47. More specifically, tissue-engaging element 30 is generally frusto-conical in shape and thus defines a narrow end 75 and a flared end 77. End 75 defines a bore 76 which is sized to fit snugly upon flexible body 20 (seen in FIG. 2). Flared end 77 provides increased volume for interior portion 78 thereof. The conical shape of tissue-engaging element 30 together with the open character of flared end 77 and interior 78 cooperate to provide a substantial tissue-engaging property for element 30. As mentioned above, the tissue-engaging elements of the present invention may be fabricated using injection molding or cold-heading techniques as desired. While a number of suitable materials may be utilized in fabricating the tissue engaging elements of the present invention suture assembly, materials such as polypropylene or the like have been found to be suitable and advantageous. Alternatively, absorbable materials may also be used.

Figure 5:
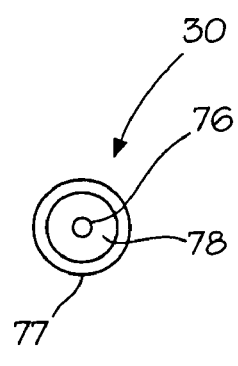
FIG. 5 sets forth a front view of the tissue-gripping element of FIG. 4.

FIG. 5 sets forth a rear view of tissue-engaging element 30 showing flared end 77 and interior 78. Also seen in FIG. 5 is the extension of bore 76 through end 75 of the tissue-engaging element.

FIG. 6 sets forth a partially sectioned side view of straight body 11 in the absence of attachment to flexible body 20. As is described above, straight body 11 is fabricated of a suitable material such as polypropylene or the like and defines a tapered end 12 forming a somewhat pointed end structure together with a connector end 13. Connector end 13 is shown in partial section and defines an internal bore 17. Bore 17 is sized to receive the end portion of flexible body 20 (seen in FIG. 1). Connector 13 secures straight body 11 to flexible body 20 through the application of a conventional crimping process once the end portion of flexible body 20 has been received within bore 17.

FIG. 7 sets forth a partially sectioned view of curved body 14. As described above, curved body 14 defines a sharp pointed end 15 and a connector end 16. Connector end 16 defines an internal bore 18 which is sized to receive the end portion of flexible body 20 (seen in FIG. 1) in a snug-fit. Curved body 14 is preferably formed of a plastic material such as polypropylene or the like. The attachment of connector end 16 to flexible body 20 to form the structure shown above in FIG. 1 is carried forward by inserting end 21 of flexible body 20 (seen in FIG. 1) into bore 18 after which a conventional crimping operation is applied to connector end 16. The very sharp point formed in end 15 facilitates the insertion of curved body 14 into skin or other tissue.

Figure 9:
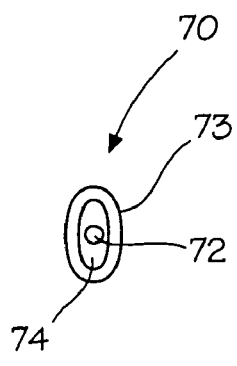
FIG. 9 sets forth a front view of the tissue-gripping element of FIG. 8.
Figure 8:
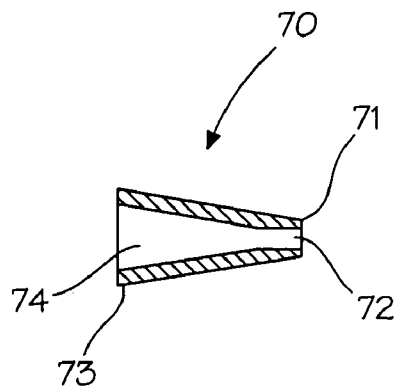
FIG. 8 sets forth a section view of an alternate embodiment tissue-gripping element.

FIGS. 8 and 9 set forth respective section and rear views of an illustrative alternate embodiment tissue-engaging element. The difference between the tissue-engaging element illustrated in FIGS. 8 and 9 and the tissue-engaging element set forth in FIGS. 4 and 5 is found in the generally elliptical cross-sectional shape rather than the circular cross-section shape found in the above-described embodiments.

More specifically, FIG. 8 sets forth a section view of an elliptically shaped tissue-engaging element generally referenced by numeral 70. Tissue engaging element 70 defines a narrow end 71 having a bore 72 formed therein. Element 70 further defines a flared end 73 and an interior 74. Element 70 is preferably fabricated utilizing injection molding or cold-heading manufacturing processes. It will be apparent to those skilled in the art that tissue-engaging element 70 provides a direct alternative replacement to tissue-engaging elements 30 through 47 shown in FIG. 1. It will be further apparent to those skilled in the art that a plurality of tissue-engaging elements such as element 70 may be utilized in the same manner as elements 30 through 47 described above. In certain applications it has been found that the elliptical cross-section of tissue-engaging element 70 provides some advantage; however, in general, the operation of tissue-engaging element 70 is substantially identical to the operation of tissue-engaging element 30 seen in FIG. 4.

FIG. 9 sets forth a rear view of tissue-engaging element 70 showing bore 72 and interior 74 formed therein. Tissue-engaging element 70 further defines a flared end 73.

Figure 10:
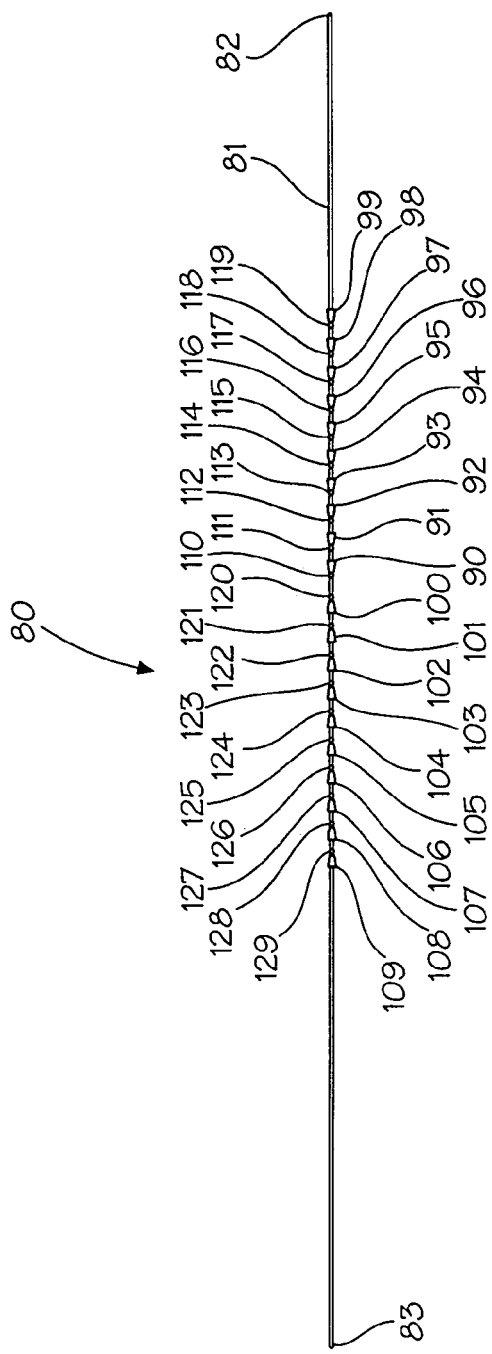
FIG. 10 sets forth a still further alternate embodiment of the present invention which provides a bidirectional suture.

FIG. 10 sets forth a side view of a still further alternate embodiment of the present invention suture generally referenced by numeral 80. It will be apparent to those skilled in the art from a comparison of the embodiment of the present invention shown in FIG. 2 and that which is shown in FIG. 10 that suture 80 provides a bidirectional suture. Suture 80 includes an elongated flexible body 81 having ends 82 and 83. A first plurality of tissue-engaging elements 90 through 99 are supported upon body 81 and are positioned by a plurality of knots 110 through 119. Knots 110 through 119 are tied as simple knots in filamentary body 81 in the manner described above. Suture 80 further includes a second plurality of oppositely facing tissue-engaging elements 100 through 109. Tissue-engaging elements 100 through 109 are positioned upon body 81 in an opposite orientation to that of elements 90 through 99. In a similar fashion to the above-described suture, a plurality of knots 120 through 129 are tied within body 81 to secure the positions of tissue-engaging elements 100 through 109. It will be apparent to those skilled in the art that the opposite orientation of tissue-engaging elements 90 through 99 from tissue-engaging elements 100 through 109 provides suture 80 with a bidirectional gripping characteristic suitable for insertion in surgical procedures where a bidirectional grip is required. It will be equally apparent to those skilled in the art from examining FIGS. 2 and 10 that alternative arrangements to the arrangements of tissue-engaging elements shown in FIGS. 2 and 10 may be utilized without departing from the spirit and scope of the present invention. In accordance with an important advantage of the present invention suture, the position of tissue-engaging elements upon the filamentary body as well as the orientation of the tissue-engaging elements may be varied or combined as desired to meet specific and particular needs in a given procedure.

Figure 11:
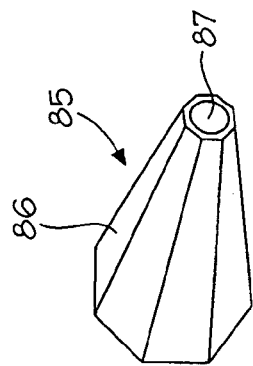
FIG. 11 sets forth a perspective view of a still further alternate embodiment of the present invention.

FIG. 11 sets forth a perspective view of a tissue-engaging element constructed in accordance with a still further alternate embodiment of the present invention. It will be recalled that FIGS. 4 and 5 above set forth a frusto-conical embodiment of the present invention tissue-engaging elements while FIGS. 8 and 9 set forth an elliptically cross-sectioned conical body forming an alternate construction for the tissue-engaging elements. FIG. 11 shows a faceted embodiment of the present invention in which the outer shape of the tapered tissue-engaging element defines a plurality of facets. Thus in FIG. 11, a tissue-engaging element 85 defines a bore 87 therethrough. Tissue-engaging element 85 is generally tapered to define a narrow end and a broader end and is covered on its outer surface by a plurality of facets 86. Tissue-engaging element 85 is suitable for substitution in any of the above-described suture assemblies and is representative of a still further alternate shape for the tissue-engaging elements of the present invention suture. Thus, it will be apparent to those skilled in the art that a variety of tissue-engaging element structures or shapes may be envisioned and utilized without departing from the spirit and scope of the present invention.

What has been shown is a novel suture assembly which provides an implantable directional camming device which may be either directional or bi-directional in fabrication. The suture assembly shown may be fabricated using injection molded or cold-headed manufacturing techniques and is suitable for use in wound closure, tissue approximation, tissue support, suspension and/or fixation. Tissue engaging elements are shown which provide either circular cross-section or elliptical cross-section. The present invention suture assembly may be inserted into the human body either with or without the use of an introducer. The present invention suture is designed to work in conjunction with the healing process post surgical. The inventive suture assembly shown holds wounds closed without the need for suture knot tying to maintain tissue approximation.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

I claim:

1. A suture comprising: a singular, uninterrupted flexible, elongate polymeric thread structure having first and second ends; a plurality of subcutaneous, tissue-engaging elements for cosmetic surgery, aesthetic surgery and soft tissue fixation, consisting of frusto-conical shapes each defining an enlarged hollow interior, each shape defining a tapered lumen including a forward bore therethrough at a narrow end of the frusto-conical shape, the tapered lumen enlarging outwardly toward a broader end of the frusto-conical shape, said tissue-engaging elements received upon said elongate flexible polymeric thread structure and, snugly fitted along the thread; and,
a plurality of protrusions formed in said polymeric thread structure; each protrusion larger than said bore, said protrusions maintaining said tissue-engaging elements in a serial arrangement on said elongate, flexible, polymeric thread structure, the frusto-conical shape of the tissue-engaging elements together with the open character of the broader end and interior of the hollow shape cooperating to provide a substantial removable tissue-engaging property for the tissue-engaging elements.

2. A suture assembly set forth in claim 1 further including: a curved end having a sharp-pointed end and a connector end joined to the first end of said elongate flexible singular, uninterrupted, polymeric thread structure; and an elongate body having a pointed end and a connector end joined to said second end of said elongate, flexible, polymeric thread structure.

3. A suture assembly of claim 1, comprising: an elongated needle body having a first pointed end and a first connector end; a curved needle body having a second pointed end and a second connector end;
an elongated, singular, uninterrupted polymeric thread structure having a first end joined to said first connector end, a second end joined to said second connector end.

4. The suture assembly set forth in claim 1 wherein said tissue-engaging elements define generally circular cross-sections.

5. The suture assembly set forth in claim 1, wherein said tissue-engaging elements define generally elliptical cross-sections.

6. The suture of claim 1, in which the suture measures about 12 cms. between each end, the suture includes about two-forty protrusions, and the distance between each protrusion is about one (1) centimeter.

7. The suture of claim 1, in which the suture is constructed of a polymeric thread, or protrusions selected from the class consisting of polyolefin, polypropylene, absorbable materials and, PDF.

8. The suture of claim 1, in which a frusto-conical shape is covered on its outer surface by a plurality of facets.

* * * * *